United States Patent
Rau

(10) Patent No.: US 8,007,842 B2
(45) Date of Patent: *Aug. 30, 2011

(54) COMPOSITION FOR INHALATION THERAPY AND METHODS OF USE

(75) Inventor: Allen H Rau, Cincinatti, OH (US)

(73) Assignee: Tower Laboratories, Ltd., Centerbrook, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/734,914

(22) Filed: Apr. 13, 2007

(65) Prior Publication Data

US 2007/0184000 A1 Aug. 9, 2007

Related U.S. Application Data

(63) Continuation of application No. 10/840,594, filed on May 7, 2004, now Pat. No. 7,220,436.

(51) Int. Cl.
*A61K 36/61* (2006.01)
*A61K 36/537* (2006.01)
*A61K 36/534* (2006.01)

(52) U.S. Cl. .................. 424/742; 424/746; 424/747

(58) Field of Classification Search .................. None
See application file for complete search history.

(56) References Cited

U.S. PATENT DOCUMENTS

| | | | |
|---|---|---|---|
| 4,568,560 A | | 2/1986 | Schobel |
| 5,041,421 A | | 8/1991 | King |
| 5,198,144 A | | 3/1993 | Ichii et al. |
| 5,238,915 A | | 8/1993 | Fuwa et al. |
| 5,382,567 A | | 1/1995 | Fuwa et al. |
| 5,401,502 A | * | 3/1995 | Wunderlich et al. .......... 424/737 |
| 5,670,159 A | * | 9/1997 | Morton et al. ................ 424/401 |
| 5,700,449 A | | 12/1997 | Katayama et al. |
| 5,948,439 A | * | 9/1999 | Forman et al. ................ 424/466 |
| 5,957,379 A | | 9/1999 | McMorrow et al. |
| 5,958,462 A | | 9/1999 | McLean |
| 5,980,880 A | | 11/1999 | Love |
| 5,993,854 A | | 11/1999 | Needleman et al. |
| 5,997,901 A | | 12/1999 | Mills |
| 6,066,337 A | | 5/2000 | Allen et al. |
| 6,180,092 B1 | | 1/2001 | Lagin |
| 6,244,265 B1 | | 6/2001 | Cronk et al. |
| 6,280,751 B1 | | 8/2001 | Fletcher et al. |
| 6,289,967 B1 | | 9/2001 | Moore |
| 6,374,044 B1 | | 4/2002 | Freidel |
| 6,413,476 B1 | | 7/2002 | Barnhart |
| 6,447,816 B1 | | 9/2002 | Vail, III et al. |
| 2002/0061831 A1 | * | 5/2002 | Kaziska et al. ................ 510/446 |
| 2003/0156981 A1 | * | 8/2003 | Mills ................................ 422/37 |

FOREIGN PATENT DOCUMENTS

CN 1147548 A * 4/1997

OTHER PUBLICATIONS

Martin et al. Herbal Medicines for Treatment of Bacterial Infections: A Review of Controlled Clinical Trials. Journal of Antimicrobial Chemotherapy. (2003). 51, 241-246.*

* cited by examiner

*Primary Examiner* — Melenie McCormick
(74) *Attorney, Agent, or Firm* — Steven B. Kelber; Berenato & White, LLC

(57) ABSTRACT

A composition for providing aromatherapy, and in particular, symptomatic relief of nasal and sinus congestion is provided in unit dosage format. The composition includes a penetrating aromatic vapor whose release from a preparation of warm water is augmented by an effervescent component which reacts in the warm water to promote release of the aromatic fragrance, or sustained over time by tableting or gelatin encapsulation. As the fragrance is inhaled, symptomatic relief is obtained. The composition of matter may be rendered ingestible, so that the warm water containing the composition is consumed following inhalation. In preferred embodiments, the release of the penetrating aromatic fragrance persists over time.

8 Claims, No Drawings

COMPOSITION FOR INHALATION THERAPY AND METHODS OF USE

This application is a continuation of application Ser. No. 10/840,594, filed May 7, 2004, allowed.

BACKGROUND OF THE INVENTION

1. Field of the Invention

This invention pertains to a composition which can be used to secure relief from congestion of the nasal passages as well as sinus congestion, by inhalation of penetrating aromatic fragrances from a warm liquid. The invention also pertains to methods of obtaining such relief, as well as related benefits of inhalation therapy.

2. Background of the Technology

The actual background of inhalation therapy is quite old. A wide variety of products have been used over the years to generate the release of aromas that are pleasant, therapeutic or otherwise beneficial, to achieve relaxation, temporary relief from upper respiratory distress, and a variety of related conditions. As just one example, candles for what is generally regarded as "aroma therapy" are widely sold in commercial markets and in spas and other businesses offering cosmetic and therapeutic benefits, with various moods said to be induced by the selection of particular fragrances. By the same token, there are a variety of products on the market that rely, in whole or in part, on the release of specific flavors and/or fragrances, to achieve their beneficial affects, in part or in whole. In addition to the candles mentioned above, a number of products are available in oil form, which generally comprises essence of the flavor or fragrance, combined with an oil that is either tolerable on the skin, ingestible, or otherwise compatible for human use. A wide variety of aroma therapy oils are known that use, among other flavors and fragrances, peppermint, eucalyptus, spearmint, camphor and rosemary. A product marketed by "Origins" under the name "Open For Business™" is intended to provide relief for nasal passages, and is available in an oil form, that employs one or more of methanol, rosemary, lavender, eucalyptus, spearmint, pine, artemisia and camphor as effective agents. Like candles, oil preparations present practical problems in use and application, are not easily used in a wide variety of locations, and are not dosage or user friendly, in that they require the use of careful monitoring of the amount used, and may not be amenable to application in a wide variety of areas.

Other products that are available in liquid form include materials intended to be added to bath water, such as Johnson's Soothing Vapor Bath® and Mentholatum Gentle Soothing Vapor Bath® as well as liquids intended to be added to a vaporizer, generally available from Vicks, under such marks as "Vapo Steam®." Other products that also require addition to a bath for effectiveness include a variety of bath salts, and a bath bomb, which is a molded effervescent bath ball. As with the oils, these products are not generally applicable for use, but require privacy. Further, their duration is short lived, and cannot be prolonged over time. In particular, an introduction to water, they immediately dissolve or otherwise release the fragrance over a very short time span.

Other products include recognized therapeutic/pharmaceutical agents, such as cough suppressants, and decongestants (cough drops, e.g., Halls® mentho-lyptus) as well as analgesics, such as TheraFlu®, which appear in the forms of lozenges or powders.

Finally, a variety of teas, which originally represent infusions of various natural substances, but may contain extracts or preparation of the isolated flavors have been known for thousands of years, examples including mint and peppermint-based teas.

All of these existing forms of therapy, which rely to a greater or lesser extent on the use of flavor and/or fragrances to bring relief of sinus and nasal congestion, have one or more practical difficulties in use. They are not generally susceptible to transportation and use anywhere. Many of them require careful measurement for dosing, and require preparation of a bath, a vaporizer, and the privacy associated therewith, for use. Many of these prior art compositions and techniques also release aroma over a very short duration—this is particularly of powders, liquids and teas, where the fragrance is released essentially immediately, and is of short duration.

A variety of U.S. patents have issued directed to these types of prior art. These include U.S. Pat. Nos. 4,568,560; 5,041,421; 5,198,144; 5,238,915; 5,382,567, 5,957,370; 5,980,880; 5,997,901; 6,180,092; 6,244,265; 6,280,751; 6,289,967; 6,374,044; 6,413,476 and 6,447,816. None of these patents address a single dosage product provided in a compact form that is easily transported, and used without regard to needs for privacy, generally anywhere, to provide for sustained release of penetrating aromatic fragrances that can relieve the symptoms associated with congestion.

Another form of inhalation therapy is addressed in U.S. Pat. No. 5,993,854, commonly assigned herewith. In this patent, the tablet is designed for introduction in a shower or other environment where it is not immersed in water, but rather it is contacted with water, to provide for release of a volatile agent. The product requires the combination of both an effervescent agent and an exothermic agent, and of course if not susceptible of use generally, in public areas.

Accordingly, it is an object of the art to provide a composition of matter that can be used to achieve at lease temporary relief of the symptoms associated with congested nasal passages and sinuses by the inhalation of penetrating aromas, in a compact solid dosage form such as a tablet, gel or the like, which can be easily transported, and used easily, everywhere, without the existing requirements for privacy, time, etc. Ideally, such materials are designed to release the penetrating aromatic material over at least a limited period of time, so that some sustained release can be achieved.

SUMMARY OF THE INVENTION

The above objects, and other objects related to the provisions of inhalation therapy materials, are met by combining one or more of a family of penetrating aromatic materials with an effervescent composition, which, when mixed in warm water, effervesces to promote release of the penetrating aromatic material. The composition is presented in dosage form, typically, in the form of a tablet, although capsules and similar formats may be used.

The penetrating aromatic material, are not confined or uniformly characterized by any single given feature or characteristic, including vapor pressure, volatility, molecular weight and the like. Penetrating aromatic materials that may be used in connection with this invention include:

| Penetrating Aromatic Materials | |
|---|---|
| Aldehyde C-6, C-7, C-8, C-9, C-10, C-11 | Geranyl Nitrile |
| Allyl Caproate | Ginger Oil |
| iso Amyl Acetate | Hydrotropic Aldehyde |
| Amyl Butyrate | indole |

| Penetrating Aromatic Materials | |
|---|---|
| Armoise Oil (cedarleaf) | Iso Bonyl Acetate |
| Anethote | Lavandin Abrialis |
| Basil Oil | Lavender Oil |
| Benzaldehyde | Methyl Cinnamate |
| Cassia Oil | Methyl Octine Carbonate |
| Camphor | Methyl Benzoate |
| Carvone (l- or d-) | Methyl Salicylate |
| Cinnamic Alcohol | Menthol |
| Cinnamic Aldehyde | Para Cresol |
| Cis 3 Hexenol/al | Peppermint Oil |
| Citral | Petitgrain Oil |
| Citronellal | Pine Oil (terpenes) |
| Clove Oil | Phenyl Acetaldehyde |
| Cornmint Oil | Rosemary Oil |
| Ethyl Acetate | Sage Oil |
| Ethyl Butyrate | Sage Oil Dalmation |
| Ethyl Caproate | Spearmint Oil |
| Eucalyptol | Styrallyl Acetate |
| Eucalyptus Oil | Tea Tree Oil |
| Eugenol | Turpentine |
| Galbanum Oil | Trans-2-cis-6 Nonadienal/ol |
| Geramium Oil | Triplal |

The penetrating aromatic components may be anhydrous derivatives, other powders, or in liquid form. In particulate or powder form, the aromatic materials are formulated together with an effervescent component, which is designed to react with release of effervescence upon introduction of the dosage form into warm water or other heated aqueous material. Although a wide variety of effervescent components are known, exemplary effervescent components include fumaric acid, sodium bicarbonate, sodium carbonate, as well as binders, lubricants and carriers, such as polyethylene glycol (PEG) sorbitol and maltodextrin. A suitable tablet can be prepared. As the dosage form of the claimed invention is intended to be introduced into heated water or other aqueous solution, and the release of penetrating aromatic agents is preferably prolonged over time, the composition is formulated to dissolve/release relatively slowly, rather than instantly. In a tablet form, this can be achieved by selection of appropriate binders and/or tablet processing conditions. In a capsule, some of the penetrating aromatic materials may be entrained in a slowly dissolving gel comprising the capsule wall. The invention may be further modified by the incorporation of colorants, fillers, and other inert materials.

DETAILED DESCRIPTION OF THE INVENTION

The invention begins with the appreciation of the importance of a compact, solid dosage form of product that is easily transported, and pre-measured for uniform dosing. The product permits the delivery of high impact aromatic materials without the preparation of shower, bath or vaporizer, without exaggerated requirements for privacy, and provides for a sustained release, where desired, of the penetrating aromatic material. Ideally, accordingly, the solid dosage form is prepared in the form of a tablet, which provides a low cost, easily used format that the ultimate consumer may simply unwrap and drop into warm water (generally, above about 100-150° F.). The temperature of the water serves only to enhance both dissolution of the tablet and release of the penetrating aromatic material. In preferred embodiments, the tablet is prepared with binders selected so as to retard dissolution of the tablet in the warm water. Tableting conditions and formulations can also be selected to retard the rate of release. For instance, it is well known to tablet formulators that increasing the hardness of tablets, either by mechanical means (increased compression forces) or by chemical means (high strength binders) will slow their dissolution time. Alternative dosage forms are also easily employed to release the aromatic material over an extended period of time. Thus, one dosage form within the invention is a gel capsule. The fragrance oils of the claimed invention may be carried in a gelatin capsule that dissolves over time. The fragrance can be either carried in a vehicle oil, which may be either mineral or vegetable oil, or in the alternative, using conventional technology, it may be micro encapsulated in an appropriate matrix that is formulated within the outer gelatin capsule of the dosage form. As the capsule dissolves in warm water, the effervescent action component is released, enhancing delivery of the penetrating aromatic material, which is released over time, as the gelatin dissolves. Conventional gelatins such as natural gelatins manufactured from bovine hides and "vegetarian" gelatins made from polymers such as hydroxypropyl methyl cellulose are known to those of skill in the art.

As discussed above, in one embodiment, the invention embraces the rapid release of penetrating vapors from the surface of the warm liquid in which the composition is placed. The effervescent component (reactants which combine, in the warm liquid, to release carbon dioxide) ensures that useful levels of penetrating aroma are released relatively quickly, nearly instantaneously. In an alternative embodiment, where the user is content to wait a short period of time (typically one to five minutes) to build up the level of vapor released, and the relief obtained, the effervescent component is unnecessary. In this embodiment, the composition is prepared to provide sustained release (a substantially constant level of vapor is released from the surface of the liquid over the period of use). This can be achieved by preparing an effervescent-free composition of sufficient density (tablets, caplets) so as to retard rapid dissolution and release of the entrained oils/aromas. In general, a density of about 1.4 g/cc or higher is required. In the alternative, a gelatin encased capsule, or gelcap, can be prepared, that is made from a slowly dissolving gelatin, with the aromatic materials contained within and/or as part of the gelatin wall of the capsule. A large variety of "softgels" are available for this use. Exemplary ones include those available from Cardinal Health of Somerset, N.J. under the brand "Scherersols." The period of release can be up to 20-30 minutes or more.

Subsequent to the making of the invention claimed herein, the inventor communicated this invention to a company which subsequently, but less than one year prior to the filing date of this application without permission, marketed the invention as "Vapor Shot". While not prior art to this invention, Vapor Shot reflects one application of the technology disclosed and claimed herein. Representative formulations are provided herewith.

Sample Formulations (%/w/w)

| Material | Effervescent Tablet | Non-Effervescent Tablet |
|---|---|---|
| Fumaric Acid | 38.0 | |
| Sodium Bicarbonate | 19.0 | |
| Sodium Carbonate | 19.0 | |
| PEG-180 | 2.0 | 1.0 |
| Sorbitol | 14.0 | |
| Dextrates | | 88.0 |
| Soy Polysaccharides | | 2.0 |
| Sodium Benzoate | | 2.0 |
| Maltodextrin | 4.0 | 3.5 |
| Silica | 0.5 | |
| Fragrance | 3.5 | 3.5 |

-continued

| Material | Effervescent Tablet | Non-Effervescent Tablet |
|---|---|---|
| Color | As desired | As desired |
| TOTAL | 100.0 | 100.0 |

As noted above, the single dosage formulation of the claimed invention is designed to be added to hot water. As the penetrating aromatic material is released, the container of hot water (cup, bowl or the like) is held in close proximity to the nose, and the penetrating aromatic material being released inhaled by the user. Clearly, the product need not be ingestible. Given the nature of the product, and the associations of some of the aromatic oils with flavors familiar to a wide spectrum of users, however, it may be desirable to render the product ingestible as well as suitable for inhalation of the penetrating vapors released. Under such conditions, care should be taken to formulate the effervescent product with materials that are safe for ingestion, and suitable flavorants may be added. For maximum performance, the product is first inhaled, and then, as the quantity of penetrating aromatic material released is reduced, the product may then be ingested as desired.

While the product may be formulated in capsule, caplets, tablet form and the like, one exemplary form, for the treatment of sinus congestion and the alleviation of symptoms associated therewith, is a single dosage tablet. The tablet is prepared using conventional tableting press equipment and processes, compressing the dry ingredients set forth below. This representative embodiment releases the penetrating and soothing vapors of mental and eucalyptus to provide immediate relief from the symptoms associated with sinus congestion.

| Component | % w/w |
|---|---|
| Citric Acid | 40.000 |
| Sodium Carbonate | 20.000 |
| Sodium Bicarbonate | 20.000 |
| PEG-180 | 2.000 |
| Silica | 0.250 |
| Maltodextrin | 2.500 |
| Sorbitol | 13.710 |
| Menthol | 0.500 |
| Eucalyptus Oil | 1.000 |
| Blue 1 Lake | 0.015 |
| Yellow 5 Lake | 0.025 |
| TOTAL | 100.000 |

While the embodiments of this invention have been illustrated as useful in the relief of sinus and nasal congestion, the invention is not so limited, and can generally be used wherever aromatherapies find application. Those of skill in the art will select from the list of penetrating aromatic components to compound formulations that offer relief other than from, or in addition to, sinus and nasal congestion symptoms. For example, many of the penetrating aromatic materials listed are purported to deliver 'emotional' benefits traditionally associated with aromatherapy. Such benefits include stress relief, refreshment, invigoration, stimulation, relaxation (and/or calming), and aid in sleeping.

The invention described above is described both generically, and by reference to specific example. The examples are not intended to be limiting, and should not be so construed, unless specifically so indicated in the claims. The invention relies on a variety of techniques known to those of skill in the art, that are not repeated in detail herein, including preparation of effervescent bases, tableting processes, the formation of capsules and micro encapsulated particles, the preparation of ingestibles and the like. Those of skill in the art will be aware of sources of information for such materials and processes, including various formulas and handbooks.

What is claimed is:

1. A composition of matter free of exothermic reactants, comprising:
   a penetrating aromatic fragrance selected from the group consisting of: Aldehyde C-6, C-7, C-8, C-9, C-10, C-11, Allyl Caproate, iso Amyl Acetate, Amyl Butyrate, Armoise Oil (cedarleaf), Anethole, Basil Oil, Benzaldehyde, Cassia Oil Camphor, Carvone (1- or d-), Cinnamic Alcohol, Cinnamic Aldehyde, Cis 3 Hexenol/al, Citral, Citronellal, Clove Oil, Cornmint Oil, Ethyl Acetate, Ethyl Butyrate, Ethyl Caproate, Eucalyptol, Eucalyptus Oil, Eugenol, Galbanum Oil, Germium Oil, Geranyl Nitrile, Ginger Oil, Hydrotropic Aldehyde, Indole, Iso Bornyl Acetate, Lavandin Abrialis, Lavender Oil, Methyl Cinnamate, Methyl Octine Carbonate, Methyl Benzoate, Methyl Salicylate, Para Cresol, Peppermint Oil, Petitgrain Oil, Pine Oil (terpenes), Phenyl Acetaldehyde, Rosemary Oil, Sage Oil, Sage Oil Dalmation, Spearmint Oil, Styrallyl Acetate, Tea Tree Oil, Turpentine, Trans-2-cis-6 Nonadienal/ol, and Triplal;
   wherein said composition further comprises an effervescent component which, when solubilized in a warm aqueous liquid, effervesces, to improve release of said penetrating aromatic fragrance from a surface of said liquid, whereby, on introduction of said composition of matter, which is in single dosage form, into said liquid, said effervescing component effervesces, and said penetrating aromatic fragrance is released from said warm liquid in a fashion sustained over the period of use so as to provide aromatherapy to an individual in need thereof inhaling said penetrating aromatic fragrance,
   wherein said composition comprises a binder which retards dissolution and sustains release of said penetrating aromatic fragrance, and said composition is in the form of a tablet having a density in excess of 1.4 g/cc wherein said fragrance release persists over a period of time of at least five minutes.

2. A method of providing aromatherapy to a human patient in need of same, comprising placing the single dosage formulation of claim 1 in a container of liquid comprising water of at least 100° F., allowing said composition to be solubilized in said water, and allowing said patient to inhale said penetrating aromatic fragrance released from said water.

3. The method of claim 2, wherein said composition in said warm water is ingestible, and subsequent to said inhalation, said patient ingests said composition.

4. The method of claim 2, wherein said process provides symptomatic relief of sinus congestion, nasal congestion or respiratory distress in said patient.

5. The method of claim 2, wherein said process provides at least one benefit selected from the group consisting of stress relief, refreshment, invigoration, stimulation, relaxation, calming and aid in sleeping to the patient.

6. The composition of claim 1, wherein said fragrance release persists over a period of at least 20 minutes.

7. The composition of claim 1, wherein said fragrance release persists over a period of at least thirty minutes.

8. A composition of matter free of exothermic reactants, comprising:

a penetrating aromatic fragrance selected from the group consisting of: Aldehyde C-6, C-7, C-8, C-9, C-10, C-11, Allyl Caproate, iso Amyl Acetate, Amyl Butyrate, Armoise Oil (cedarleaf), Anethole, Basil Oil, Benzaldehyde, Cassia Oil Camphor, Carvone (1- or d-), Cinnamic Alcohol, Cinnamic Aldehyde, Cis 3 Hexenol/al, Citral, Citronellal, Clove Oil, Cornmint Oil, Ethyl Acetate, Ethyl Butyrate, Ethyl Caproate, Eucalyptol, Eucalyptus Oil, Eugenol, Galbanum Oil, Germium Oil, Geranyl Nitrile, Ginger Oil, Hydrotropic Aldehyde, Indole, Iso Bornyl Acetate, Lavandin Abrialis, Lavender Oil, Methyl Cinnamate, Methyl Octine Carbonate, Methyl Benzoate, Methyl Salicylate, Para Cresol, Peppermint Oil, Petitgrain Oil, Pine Oil (terpenes), Phenyl Acetaldehyde, Rosemary Oil, Sage Oil, Sage Oil Dalmation, Spearmint Oil, Styrallyl Acetate, Tea Tree Oil, Turpentine, Trans-2-cis-6 Nonadienal/ol, and Triplal;

wherein said composition further comprises an effervescent component which, when solubilized in a warm aqueous liquid, effervesces, to improve release of said penetrating aromatic fragrance from a surface of said liquid, whereby, on introduction of said composition of matter, which is in single dosage form, into said liquid, said effervescing component effervesces, and said penetrating aromatic fragrance is released from said warm liquid in a fashion sustained over the period of use so as to provide aromatherapy to an individual in need thereof inhaling said penetrating aromatic fragrance, wherein said composition comprises a binder which retards dissolution and sustains release of said penetrating aromatic fragrance, and said composition is in the form of a tablet having a density in excess of 1.4 g/cc, wherein said composition, when dissolved in water, is edible.

* * * * *